United States Patent [19]

Kubodera et al.

[11] Patent Number: 4,888,163

[45] Date of Patent: Dec. 19, 1989

[54] DIAGNOSTIC AGENT FOR BREAST CANCER OR TUMOR

[75] Inventors: Akiko Kubodera, Chiba; Touichi Tanaka; Yukimichi Komori, both of Tokyo, all of Japan

[73] Assignee: Nihon Medi-Physics Co., Ltd., Hyogo, Japan

[21] Appl. No.: 301,134

[22] Filed: Jan. 25, 1989

[30] Foreign Application Priority Data

Jan. 29, 1988 [JP] Japan .................................. 63-20379

[51] Int. Cl.[4] ...................... A61K 49/02; G01N 33/53
[52] U.S. Cl. .......................................... 424/1.1; 424/9; 530/402; 436/547; 436/548
[58] Field of Search ..................... 424/1.1, 9; 530/402; 436/548, 547

[56] References Cited

U.S. PATENT DOCUMENTS 4,740,476  4/1988  Kubodera et al. .

FOREIGN PATENT DOCUMENTS 178683  4/1986  Japan .

OTHER PUBLICATIONS

Komori Y., et al., Japanese Journal of Nuclear Medicine, vol. 24, No. 8, pp. 47, 1200 and 1302 (8/20/87) and translation.

Primary Examiner—John S. Maples

[57] ABSTRACT

A radioactive diagnostic agent for imaging a breast cancer or tumor, which comprises an anti-estriol-3-sulfate antibody labeled with a radioisotope as an essential component.

5 Claims, 2 Drawing Sheets

DIAGNOSTIC AGENT FOR BREAST CANCER OR TUMOR

The present invention relates to a diagnostic agent for cancer or tumor. More particularly, it relates to a radioactive diagnostic agent for imaging of breast cancer or tumor and an imaging method of breast cancer or tumor with the same.

For the non-invading nuclear medical diagnosis of cancer or tumor, there is ordinarily used gallium citrate $^{67}$Ga). While gallium citrate ($^{67}$Ga) has an accumulating property on cancer or tumor cells, it simultaneously possesses the following disadvantages: (1) since its specificity to cancer or tumor cells is low and its energy characteristics are not proper, clear and sharp scintigraphy is hardly obtainable; (2) it takes a long time until the radioactivity disappears from the entire body so that many days are needed for the examination; and (3) its half life is so long as 78.1 hours, and the amount of exposure dose against the patient can not be disregarded. Because of the above reason, many researches have been made for development of an imaging agent having a higher specificity to cancer or tumor cells so as to make possible the quick examination.

One of the recent proposals is imaging of cancer or tumor by a radioisotope-labeled antibody with a high specificity to any marker related to cancer or tumor. Since the large scale production of a monoclonal antibody having a high specificity to cancer or tumor by cell culture of a hybridoma obtained from the cell fusion between an antibody-producing cell and a myeloma cell, was reported by Milstein et al. (Nature, Vol. 256, p. 495 (1975)), various antibodies specific to cancer or tumor-related antigens have been produced, and imaging of cancer or tumor using the thus produced monoclonal antibodies has been made. The imaging technique by the use of said radioisotope-labeled antibody is generally called a "radioimmunosintigraphy". However, this technique still includes various problems. For instance, the radioisotope-labeled antibody takes a long time for accumulation on cancer or tumor and the up-take ratio is low. Further, for instance, the accumulation is made not only on cancer or tumor but also on other normal organs and tissues, and the disappearnce of its radioactivity from such other organs and tissues takes a long time. Due to these reasons, it could not be placed under the practical use.

On the other hand, studies on the diagnosis of breast cancer or tumor have been made actively with such substances specific to steroid hormone receptors as radioactive iodine-labeled estradiol derivatives (Hanson et al.: American Chemical Society Meeting, Aug. 3–28, 1981, Reference N.U.S.L. 56; Kabalka: Applications of Nuclear and Radiochemistry, Lambrecht, R. M. Morcosn., Eds., Newark, N.J., Pergamon Press, 1981, Chap. 17; JP-A-60-78995). In order to achieve a relaiable diagnosis with these receptor-specific substances, those substances are required to satisfy the following conditions: (1) they have high affinity and specificity to the receptor; (2) their specific radioactivity is sufficiently high; and (3) their labeling nuclide is not liberated in living bodies. However, any radioactive receptor-specific substance satisfying all these conditions has not been developed.

SUMMARY OF THE INVENTION

As a result of the extensive study, it has now been found that an anti-estriol-3-sulfate antibody labeled with a radioisotope shows good accumulation at breast cancer or tumor with a significantly high up-take ratio relative to normal organs or tissues. This invention is based on the above finding.

DETAILED DESCRIPTION OF THE INVENTION

Figure 1:
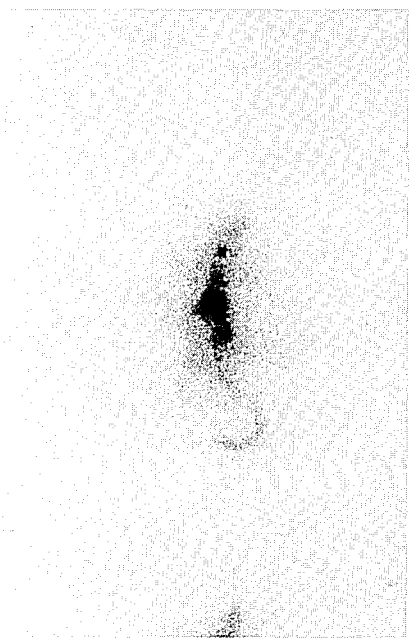
FIGS. 1–4 are scintigrams referred to in Example 7.

According to the present invention, there is provided an imaging agent for breast cancer or tumors, which comprises as an essential agent an anti-estriol-3-sulfate antibody labeled with a radioisotope (e.g. iodine $^{123}$I, iodine $^{131}$I, gallium-67, gallium-68, thallium-201, indium-111, technetium-99m, etc.).

Estriol-3-sulfate (hereinafter referred to as "E$_3$-3S") is a metabolite of estriol, and an anti-estriol-3-sulfate antibody (hereinafter referred to as "E$_3$-3S antibody") can be produced by administering parenterally a conjugate substance comprising E$_3$-3S acting as a hapten to a living body for sensitization. Labeling of the E$_3$-3S antibody with a radioisotope may be made by a per se conventional procedure. Advantageously, the radioisotope-labeled E$_3$-3S antibody to be used as the imaging agent in the invention is not necessarily required to have a high specific radioactivity, and therefore its production can be made with ease.

The E$_3$-3S antibody can be produced, for instance, by the process as disclosed in U.S. Pat. No. 4,740,476. Namely, it may be produced in a living body chosen from a vertebrate animal (e.g. cattle, horse, sheep, goat, rabbit, rat, mouse) by parenteral administraiton of a E$_3$-3S-protein conjugate of the formula:

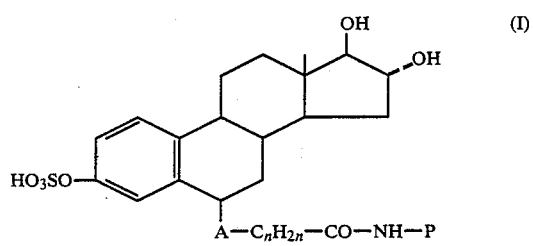

wherein A is =N—O—or —O—CO—, n is an integer of 1 to 4 and —NH—P is the residue of a protein excluding a hydrogen atom in the amino form therefrom (hereinafter referred to as "ESP conjugate"). Then, a humor or body fluid (e.g. blood) is taken from the living body, optionally followed by removal of impurities. Usually, a serum containing the E$_3$-3S antibody, i.e. an anti-serum, is employed.

Also, the monoclonal antibody specific to E$_3$-3S as produced by application of the Milstein et al. procedure for preparation of a monoclonal antibody (Nature, Vol. 256, 495–497 (1975)) using the ESP conjugate is usable. The chimeric antibody obtined from any of the above antibodies as well as the human type antibody are further usable.

Labeling of the antibody with a radioisotope may be effected by any appropriate conventional procedure depending on the kind of the radioisotope. For instance, labeling with radioactive iodine may be carried out by the chloramin T method, the iodine chloride method, the lactoperoxidase method, the iodogen method or the like (cf. "Experimental Procedures for Metabolism of Radio-isotope-labeled Medicines", published by Maruzen on Jan. 30, 1981, pages 95–101). Further, for instance, labeling with any other radioisotope may be accomplished by first coupling the antibody with a bifunctional chelate compound (e.g. diethylenetrimainepentaacetic acid cyclic anhydride, ethylenediaminetetraacetic acid succinimide ester, deferoxamine (JP-A- No. 56-125317), 1-(p-aminoalkyl)-phenylpropane-1,2-dione-bis(thiosemicarbazone) derivatives (JP-A- No. 59-193870), etc.) by the carbodiimide method, the acid anhydride method, the glutaraldehyde method or the like and treating the resultant coupling product with the radioisotope. On labeling with technetium-99m, a pertechnetate ($^{99m}TcO_4^-$) is to be treated with a reducing agent such as stannous chloride, stannous fluoride, stannous nitrate) so as to lower the atomic valency (e.g. III, IV or V) of technetium for formation of a stable chelate complex.

The diagnostic agent of the invention may be administered parenterally, particularly intravenously, to patients. The diagnostic agent should have sufficient radioactivity and radioactivity concentration which can assure reliable diagnosis. For instance, in case of the radioisotope being technetium-99m, it may be included usually in an amount of 0.1 to 50 mCi in about 0.5 to 5.0 ml on administration. The diagnostic agent may be administered immediately after the preparation, but it is favorable to have such a stablility as can be stored for an appropriate time after the preparation. When desired, the diagnostic agent may contain any additive such as a pH controlling agent (e.g. acid, base, buffer), a stabilizer (e.g. ascorbic acid) or an isotonizing agent (e.g. sodium chloride).

Practical and presently preferred embodiments of the invention are illustratively shown in the following Examples.

EXAMPLE 1

Preparation of the $E_3$-3S antibody:

The 6-oxoestriol-3-sulfate-O-carboxymethyloxime-BSA conjugate (I) (0.5 mg) was dissolved in a sterilized isotonic saline solution (0.25 ml) and emulsified with Freund complete adjuvant (0.25 ml). The emulsion was subcutaneously injected into a guinea pig at each thigh and below each shoulder blade. The subcutaneous injection was repeated 14 and 28 days after the initial injection and every 30 days thereafter. Ten days after the booster injection, the blood was taken from the animal. The serum was separated by centrifugation at 3500 r.p.m. for 20 minutes and stored at $-25°$ C.

EXAMPLE 2

Purification of the $E_3$-35S antibody

To the anti-serum (300 μl) as obtained in Example 1, a phosphate buffer physiological saline solution (phosphate buffer solution, 0.01 M; pH, 7.5 (hereinafter referred to as PBS)) (300 μl) was added, and 50 % ammonium sulfate solution (pH, 7.5) (600 μl) was added thereto, followed by allowing to stand at 4° C. for 1 hour. The resultant mixture was subjected to centrifugation at 8,000 rpm for 20 minutes. The supernatant was removed, and the precipitate was collected. To the collected precipitate, 50 % ammonium sulfate solution (600 μl) was added, and the resultant mixture was allowed to stand at 4° C. for 1 hour and then centrifuged under the same condition as above. This operation was repeatedly carried out twice. To the precipitate, PBS (1 ml) was added, and the resultant solution was dialyzed to PBS at 4° C. overnight, followed by freeze-drying to give the $E_3$-3S antibody in a purified state.

EXAMPLE 3

Preparation of the $^{125}I$-labeled $E_3$-3S antibody:

The $E_3$-3S antibody (5 μg) as obtained in Example 2 was dissolved in 0.05 M phosphate buffer (pH, 7.5) (25 μl), $Na^{125}I$ (200 μCi) and chloramin T (20 μg) as an oxidizing agent were added thereto, and the resultant mixture was stirred at 0° C. for 15 seconds, followed by addition of sodium metabisulfite (200 μg) and potassium iodide (2 mg). The resultant mixture was subjected to gel filtration using Cephadex G-25, and the fraction having radioactivity were collected to give the $^{125}I$-labeled $E_3$-3S antibody.

EXAMPLE 4

Preparation of the $^{131}I$-labeled E -3S antibody

In the same manner as in Example 3 but using the $E_3$-3S antibody (25 μg), $Na^{131}I$ (1 mCi), chloramin T (100 μg), sodium metabisulfite (1 mg) and potassium iodide (10 mg), there was obtained the $^{131}I$-labeled $E_3$-3S antibody.

EXAMPLE 5

Preparation of the $^{111}In$-labeled $E_3$-3S antibody:

The $E_3$-3S antibody (5 mg) as obtained in Example 2 was dissolved in 0.05 M phosphate buffer (pH, 7.5) (2 ml), diethylenetriaminepentaacetic acid cyclic anhydride (hereinafter referred to as "DTPA") in a an amount of 10 times by mol was added thereto, and the resultant mixture was stirred at room temperature overnight. The resultant solution was dialyzed to 1 M sodium chloride solution and 0.9 % physiological saline solution and equilibrated with physiological saline solution, followed by purification with Sephadex G-25. To the thus obtained $E_3$-3S antibody-DTPA conjugate solution, indium chloride ($^{111}InCl_3$) (1 mCi) was added, and the mixture was allowed to stand for 15 minutes to give a solution comprising the $^{111}IN$-labeled $E_3$-3S antibody-DTPA conjugate.

EXAMPLE 6

Biodistribution of the $^{125}I$-labeled $E_3$-3S antibody in breast cancer-induced rat To each of SD strain female rats, 10 mg of a sesame oil suspension of 7,12-dimethylbenzanthracene (hereinafter referred to as "DMBA") (10 mg/ml) were orally administered, and one week thereafter, the same amount of the suspension was again administered for induction of breast cancer. About 60 to 90 days after the DMBA administration, the breast cancer induction was confirmed, and the animals were then used for the test. The $^{125}I$-labeled $E_3$-3S antibody solution (1.5 μCi) as obtained in Example 1 was intravenously administered to each of the breast cancer-induced rats (bodyweight, about 159 g) as above through the tail vein. After 48 hours, the animals were sacrificed, and various organs were taken out. The radioactivity and the weight were measured for each organ, and the radioactivity percentage per unit weight (% ID/g) was calculated.

To some of the breast cancer-induced rats 24 hours after said administration of the $^{125}$I-labeled E$_3$-3S antibody, the 2nd antibody to the E$_3$-3S antibody (the IgG fraction of the goat serum to the anti-guinea pig IgG) (25 μg) in a physiological saline solution (200 μl) was intravenously administered, and 24 hours thereafter, they were sacrificed, and the organs taken from them were subjected to examination in the same manner as above.

The results are shown in Table 1.

TABLE I (Biodistribution of $^{125}$I-labeled E$_3$-3S antibody in breast cancer-induced rat, % ID/g × 10$^{-1}$)

| Organ | Breast cancer-induced rat | Breast cancer-induced rat (2nd antibody given) |
|---|---|---|
| Brain | 0.2 ± 0 | 0.2 ± 0 |
| Heart | 1.1 ± 0.1 | 0.8 ± 0.2 |
| Lung | 1.9 ± 0.2 | 1.2 ± 0.5 |
| Liver | 2.4 ± 0.7 | 1.6 ± 0.2 |
| Spleen | 1.3 ± 0.4 | 1.3 ± 0.4 |
| Adrenal gland | 1.8 ± 0.5 | 1.3 ± 0.5 |
| Kidney | 3.1 ± 0 | 2.6 ± 0.4 |
| Ovary | 2.4 ± 0.1 | 2.4 ± 1.1 |
| Uterus | 2.0 ± 0.1 | 2.3 ± 0.6 |
| Bone | 1.0 ± 0.4 | 1.0 ± 0.2 |
| Blood | 4.6 ± 0.6 | 2.6 ± 0.6 |
| Breast cancer | 3.5 ± 0.8 | 4.3 ± 1.0 |

Note:
Mean ± standard deviation (n = 3)

As understood from the above, the $^{125}$I-labeled E$_3$-3S antibody shows sufficiently higher accumulation in breast cancer than in other organs, and it is extremely useful for the purpose of nuclear medicine diagnosis.

When the 2nd antibody was administered, the accumulation rate per gram tissue in other organs decreased, while that in breast cancer increased. Namely, the breast cancer-to-blood ratio increased about 4 times, and the breast cancer-to-other organ ratio also increased significantly. It is thus understood that the administration of the 2nd antibody after administration of the $^{125}$I-labeled E$_3$-3S antibody produces the increase of the breast cancer-to-other organ ratio so that clear and sharp imaging is realized.

EXAMPLE 7

Scintigraphy of the $^{131}$I-labeled E$_3$-3S antibody in breast cancer-induced rat The $^{131}$I-labeled E -3S antibody (120 μCi) as obtained in Example 2 was administered intravenously to normal rats and breast cancer-induced rats as in Example 3. After 48 and 72 hours, scintigram was obtained by a gamma camera ("LFOV" manufactured by Shimadzu Seisakusho). After 24 hours from the administration of the $^{131}$I-labeled E$_3$-3S antibody, the 2nd antibody (1.5 mg/200 ml physiological saline solution) was administered to the breast cancer-induced rats. Also, a potassium iodide solution (10 mg/ml) was administered orally to the animals 24 hours before the administration of $^{131}$I-labeled E$_3$-3S antibody for preventing the accumulation of free $^{131}$I ion on the thyroid gland.

Figure 2:
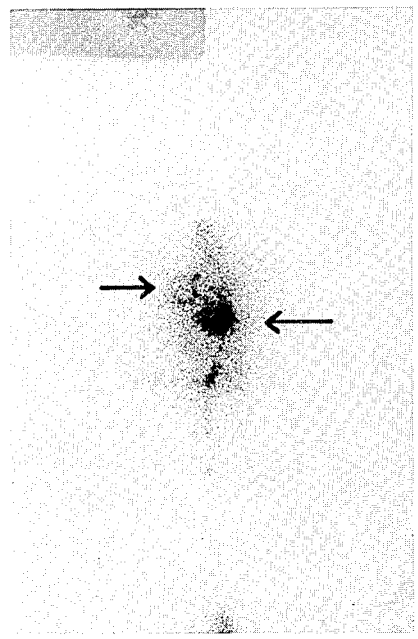
Figure 3:
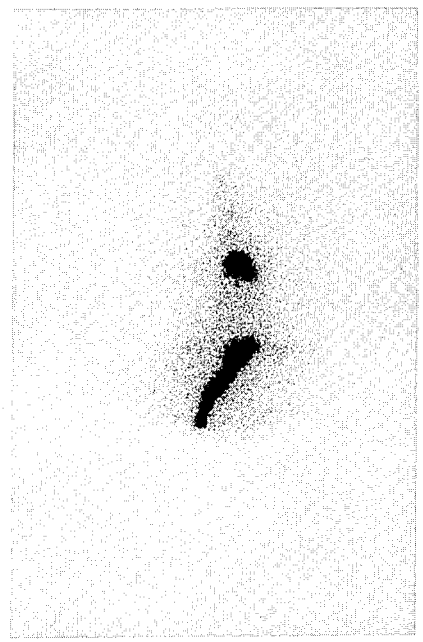
Figure 4:
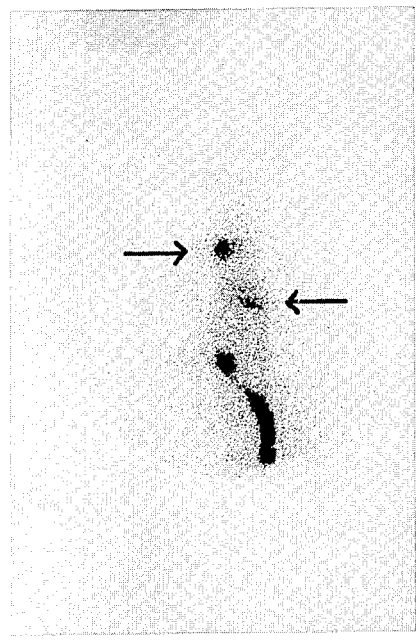

FIGS. 1, 2, 3 and 4 of the accompanying drawings show respectively the whole body scintigram of the normal rat 48 hours after the administration, the whole body scintigram of the breast cancer-incuded rat 48 hours after the administration, the whole body scintigram of the normal rat 72 hours after the administration and the whole body scintigram of the breast cancer-incuded rat 72 hours after the administration. Blacking at the lower parts of FIGS. 3 and 4 indicates the residual radioactivity due to the mistake on the tail vein administration, and it does not show any specific accumulation of $^{125}$I-labeled E$_3$-3S antibody. Each arrowline indicates the existence of a breast cancer.

Imaging of the breast cancer was recognized 48 hours after the administration, and only the breast cancer could be imaged as a hot spot after 72 hours to giva a very clear scintigram. From this fact, it may be understood that the diagnostic agent of the invention is very useful for the diagnosis of breast cancer.

What is claimed is:

1. A radioactive diagnostic composition for imaging breast cancer or tumor, which comprises an anti-estriol-3-sulfate antibody labeled with a radioisotope which composition does not contain estriol-3-sulfate.

2. The diagnostic composition according to claim 1, wherein the anitbody is a monoclonal antibody.

3. The diagnostic composition according to claim 1, wherein the radioisotope is chosen from iodine-131, iodine-123, gallium-67, gallium-68, thallium-201, indium-111 and technetium-99m.

4. A method for imaging a breast cancer or tumor in a living body, which comprises administering parenterally to the living body an effective amount of a radioactive diagnostic composition which comprises an anti-estriol-3-sulfate antibody labeled with a radioisotope allowing the radioactive diagnostic composition to accumulate at the breast cancer or tumor and subsequently imaging the breast cancer or tumor to detect the radioactivity accumulated thereat.

5. The method according to claim 4, wherein the imaging is effected by scintigraphy.

* * * * *